United States Patent [19]
Shinoda et al.

[11] Patent Number: 4,784,152
[45] Date of Patent: Nov. 15, 1988

[54] PULSE WAVE DETECTING APPARATUS

[75] Inventors: Masayuki Shinoda, Tajima, Japan; William A. Ogletree, Newtown Square, Pa.

[73] Assignee: Colin Electronics Co., Ltd., Aichi, Japan

[21] Appl. No.: 137,347

[22] Filed: Dec. 23, 1987

[30] Foreign Application Priority Data

May 2, 1987 [JP] Japan .................. 62-109594

[51] Int. Cl.⁴ .............................................. A61B 5/02
[52] U.S. Cl. .................................................. 128/690
[58] Field of Search ............... 128/687, 688, 689, 690

[56] References Cited

U.S. PATENT DOCUMENTS 4,307,728 12/1981 Walton .............................. 128/687
4,409,983 10/1983 Albert ............................... 128/490

FOREIGN PATENT DOCUMENTS 60901 4/1986 Japan .

Primary Examiner—Alan Cohan
Attorney, Agent, or Firm—Parkhurst, Oliff & Berridge

[57] ABSTRACT

A pulse wave detecting apparatus for detecting a blood pressure pulse wave of an arterial vessel of a subject, based on an oscillatory motion of at least one contact element which is adapted to be depressed against a surface of a body member of the subject, such that each contact element is iscillated in response to the pulsation of the arterial vessel. The apparatus includes a main frame for supporting each contact element such that the contact element is movable relative to the main frame fixed in position on the surface of the body member. A positioning device is provided, which is capable of at least moving the contact element relative to and along the body surface, in a direction perpendicular to the arterial vessel, to thereby locate one of the at least one contact element right above the arterial vessel. A pressing device is provided for moving each contact element relative to the main frame, in a direction toward the surface, for forcing each contact element against the surface.

12 Claims, 3 Drawing Sheets

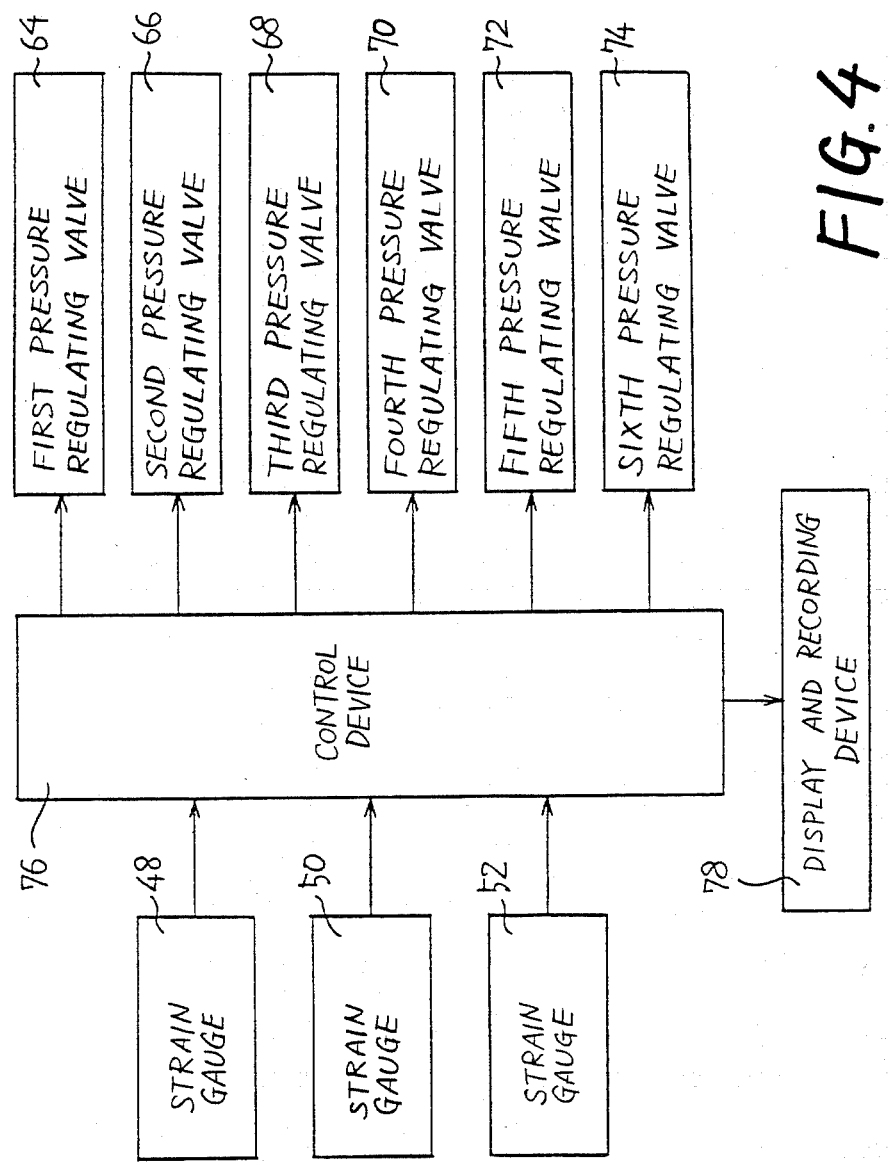

PULSE WAVE DETECTING APPARATUS

BACKGROUND OF THE INVENTION

1. Field of the Invention

The present invention relates generally to a pulse wave detecting apparatus, and more particularly to an apparatus capable of highly accurate detection of a pulse wave based on pulsations of an arterial vessel.

2. Discussion of the Prior Art

Blood pressure pulsations which are produced by heartbeats of a living being and which propagate through arteries, or pulsations of the arterial vessel walls, are generally referred to simply as "pulse wave". It is known in the art that detecting such a pulse wave of a living body provides various medical information such as a working condition of the heart of the living being. To detect the pulse wave, there is available a detecting apparatus which has a presser or contractor member which is pressed against a portion of a skin or epidermal tissue of the human being which is right above an arterial vessel. The pressure member has a contact element which is vibrated due to blood pressure pulsations of the arterial vessel. The detecting apparatus includes a converter such as a strain gauge or piezoelectric element, which converts the vibrations of the contact element caused by the pulsations of the arterial vessel, into electric signals as an output of the apparatus. An example of this type of detecting apparatus is disclosed in laid-open publication No. 61-60901 of Japanese Utility Model Application.

The contact element of the presser member of the detecting apparatus indicated above must be accurately positioned in place right above the artery, in order that the pulse wave is sensed with a high level of precision. Usually, the positioning of the contact element on the human being is manually conducted by an operator, who holds the frame or support structure holding the presser member, and places the frame into position on the appropriate portion of the human being, by way of visual inspection. This procedure does not necessarily permit the contact element to be exactly positioned right above the arterial vessel. Alternatively, the presser member is provided with a plurality of contact elements each of which is sufficiently smaller in size than the diameter of the arterial vessel. In this case, the detecting apparatus is positioned such that the contact elements are arranged in a direction perpendicular to the vessel. In operation, the most optimally located one of the contact elements is selected based on the vibrating conditions of the individual contact elements. In this case, it is difficult to manufacture the pressure member with the relatively small contact elements, and the converter which is required to convert the vibrations of all the contact elements into electric signals. Further, the sensitivity of the detecting apparatus is lowered as the size of the converter is reduced.

SUMMARY OF THE INVENTION

The present invention was developed in light of the foregoing problem experienced in the prior art. It is therefore an object of the present invention to provide a pulse wave detecting apparatus which can be readily positioned such that contact elements of a presser member are located right above an arterial vessel, in order to assure highly accurate detection of a pulse wave of the vessel.

The above object can be attained according to the principle of the present invention, which provides a pulse wave detecting apparatus for detecting a blood pressure pulse wave of an arterial vessel of a subject, based on an oscillatory motion of at least one contact element which is adapted to be depressed against a surface of a body member of the subject, such that the above-indicated at least one contact element is oscillated in response to the pulsation of the arterial vessel, the detecting apparatus comprising: (a) a main frame for supporting the at least one contact element such that the at least one contact element is movable relative to the main frame, the main frame being attached to the surface of the body member; (b) positioning means operable at least for moving the at least one contact element relative to and along the surface of the body member, in a direction perpendicular to a direction of extension of the arterial vessel, to thereby locate one of the at least one contact element right above the arterial vessel; and (c) pressing means for moving the at least one contact element relative to the main frame, in a direction toward the surface of the body member for forcing the at least one contact element against the surface of the body member.

In the pulse wave detecting apparatus of the present invention constructed as described above, the at least one contact element is disposed movably relative to the main frame which is fixedly attached to the surface of the body member of the living subject such as a human being, so that one of the at least one contact element is located right above the arterial vessel, by the positioning means. In this condition, the at least one contact element is depressed against the surface of the body member. Since the above-indicated one contact element is aligned right above the arterial vessel, the blood pressure pulse wave generated by the vessel can be accurately sensed by the contact element. Further, in the instant arrangement wherein one of the at least one contact element is positioned right above the arterial vessel, the contact element or elements may have a larger size, than in a conventional arrangement in which a multiplicity of contact elements fixed to the main frame are arranged in the direction perpendicular to the arterial vessel. In the latter case, the size of the contact elements must be comparatively small so that one of the contact elements is always located right above the arterial vessel when the main frame is attached to the body member. The comparatively larger size of the contact element or elements of the detecting apparatus according to the invention means easier manufacture of the contact element or elements, and improved detecting accuracy or sensitivity of the apparatus.

The present detecting apparatus may be operable with a single contact element. In this case, the contact element can be located right above the arterial vessel, by observing the oscillating condition of the contact element, for example, by monitoring a variation in the amplitude of a pulse wave which is obtained based on the oscillation of the contact element, while the contact element is moved by the positioning means in the direction perpendicular to the arterial vessel. However, it is preferable to provide three or more contact elements which are arranged in a plane parallel to the surface of the body member, in spaced-apart relation with each other in the direction perpendicular to the arterial vessel. In this instance, one of the three or more contact elements is brought into the pulse wave detecting position right above the arterial vessel, based on oscillating conditions of all the contact elements. If three contact elements are provided, for example, the intermediate contact element is located right above the arterial vessel. In the case where the intermediate contact element is dislocated out of position due to a movement of the body member of the subject in the process of continuously detecting the pulse wave of the artery, the direction of dislocation of the intermediate contact element an be determined based on the oscillating condition of the intermediate contact element, as compared with those of the two outer contact elements. Accordingly, the intermediate contact element can be readily relocated into position.

Even when the contact element is exactly aligned with the arterial vessel, the oscillating condition of the contact element, namely, the amplitude or other parameters of a pulse wave representing the oscillation of the contact element, tends to vary depending upon the position of the contact element in the direction parallel to the arterial vessel, and also depending upon the posture of the contact element relative to the artery, because of the presence of a bone and hypodermal tissue of the body member. In view of this tendency, it is desirable that the positioning means is capable of moving the at least one contact element in the direction parallel to the arterial vessel, and adjusting the angle of inclination of the at least one contact element in a plane perpendicular to the arterial vessel, as well as moving the at least one contact element in the direction perpendicular to the vessel.

BRIEF DESCRIPTION OF THE DRAWINGS

The above and optional objects, features and advantages of the present invention will be better understood by reading the following detailed description of presently preferred embodiments of the invention, when considered in connection with the accompanying drawings, in which:

FIG. 4 is a schematic block diagram showing a control system of the apparatus of FIG. 1.

DETAILED DESCRIPTION OF THE PREFERRED EMBODIMENTS

Figure 1:
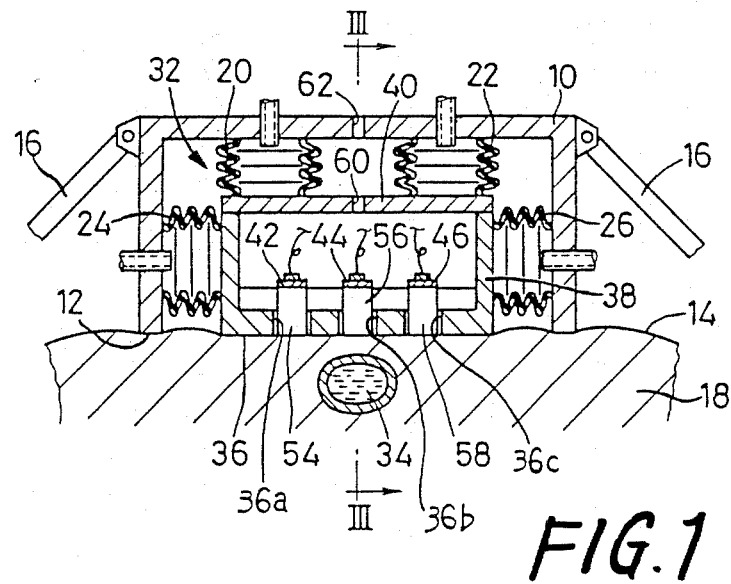
FIG. 1 is an elevational view in longitudinal cross section of one embodiment of a pulse wave detecting apparatus of the present invention.
Figure 2:
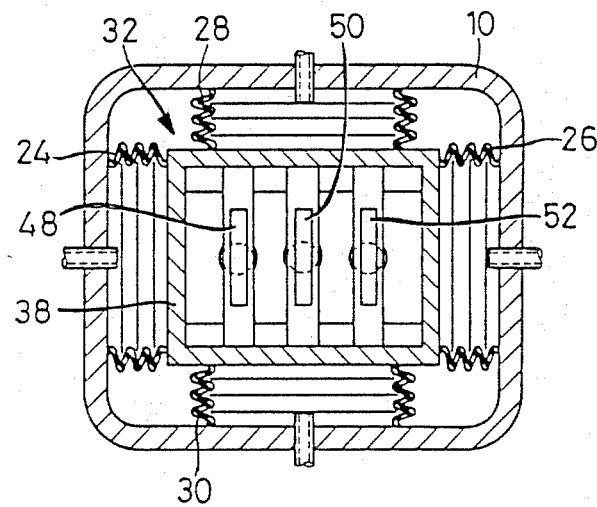
FIG. 2 is a cross sectional view taken in a plane perpendicular to the plane of FIG. 1.
Figure 3:
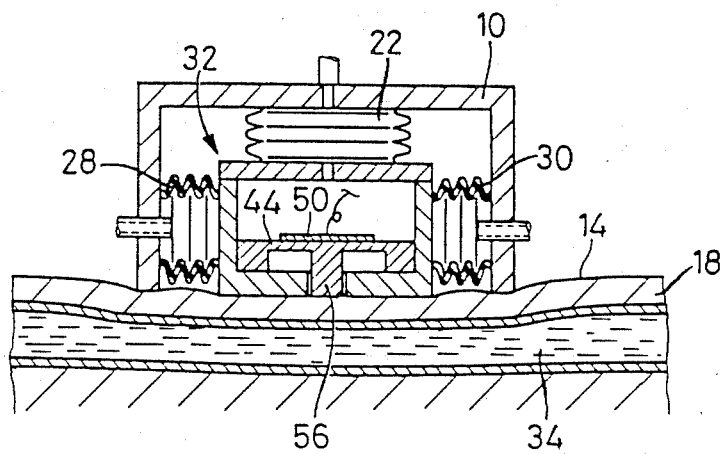
FIG. 3 is a cross sectional view taken along line III—III of FIG. 1.

Referring first to FIGS. 1-3, reference numeral 10 designates a box-like main frame of a pulse wave detecting apparatus, which has an opening 12 at its lower end. The apparatus is provided with straps or bands 16 secured to the housing 10, so that the apparatus is removably held on a skin 14 of a wrist 18 of a human being such that the lower end face defining the opening 12 is held in contact with the skin of the wrist 18. The main frame 10 accommodates a presser member 32 which is supported by six bellows 20, 22, 24, 26, 28 and 30 also accommodated in the housing 10, such that the presser member 32 is movable relative to the main frame 10. In use, the housing frame 10 is positioned on the wrist 18 such that the presser member 32 is located just above the radial artery 34. The presser member 32 includes a box-like housing member 38 which has a bottom wall 36 adapted to contact the skin 14 of the wrist 18, and a lid member 40 which closes an upper open end of the housing member 38. These housing member 38 and lid member 40 cooperate with each other to provide a housing structure of the presser member 32. Within this housing structure, there are disposed three oscillating plates 42, 44 and 46.

The oscillating plates 42, 44, 46 are disposed in a plane parallel to the bottom wall 36, and are spaced apart from each other in a direction perpendicular to the direction of extension of the radial artery 34, when the main frame 10 of the instant apparatus is set on the wrist 18. As is apparent from FIG. 3 which shows the oscillating plate 44 by way of example, each of the three oscillating plates 42, 44, 46 has relatively thick lateral end portions at which the plate is secured to the housing member 38, and a relatively thin inner portion which is elastically deformable and displaceable in a direction of thickness. To convert displacements of the thin inner portions of the oscillating plates 42, 44, 46 into electric signals, strain gauges 48, 50, 52 are provided on the upper surfaces of the oscillating plates 42, 44, 46. Each oscillating plate 42, 44, 46 has a contact element 54, 56, 58 as an integral part thereof, which extends from the lower surface of the thin inner portion indicated above. Each contact element 54, 56, 58 takes the form of a cylinder whose diameter is smaller than that of the radial artery 34. The contact elements 54, 56, 58 extend through holes 36a, 36b, 36c formed through the thickness of the bottom wall 36 of the housing member 38, such that there exists a small clearance between each contact element and the surface defining the corresponding hole. Accordingly, the contact elements 54, 56, 58 may be displaced in the vertical direction relative to the bottom wall of the housing member 38. The oscllating plates 42, 44, 46 are so dimensioned and positioned such that the free ends of the contact elements 54, 56, 58 are substantially flush with the lower end face of the housing member 38, so that the ends contact the skin 14 when the detecting apparatus is set on the wrist 18. The substantially enclosed space within the housing structure 38, 40 of the presser member 32 communicates with the ambient atmosphere, through an aperture 60 formed through the lid member 40, and an aperture 62 formed through the top wall of the main frame 10. These apertures 60, 62 permit the contact elements 54, 56, 58 of the oscillating plates 42, 44, 46 to be oscillated with high sensitivity, in response to the blood pressure pulsations of the radial artery 34.

Each of the bellows 20, 22, 24, 26, 28 and 30 is airtightly secured at its opposite ends, to the inner surface of the main frame 10 and the outer surface of the housing structure 38, 40 of the presser member 32. These bellows 20, 22, 24, 26, 28 and 30 communicate with respective conduits, through which are applied air pressures which are controlled by corresponding pressure regulating valves 64, 66, 68, 70, 72 and 74 illustrated in FIG. 4. These pressure regulating valves are connected to a suitable pressure source not shown. The two bellows 20 and 22 are interposed between the inner surface of the upper wall of the main frame 10 and the upper surface of the top wall of the housing structure of the presser member 32 (i.e., upper surface of the lid member 40). The bellows 20, 22, which are supplied with the pressurized air streams from the first and second valves 64, 66, function to bias the presser member 32 relative to the main frame 10 in the direction toward the skin 14, so that the bottom wall 36 and the contact elements 54, 56, 58 are forced against the skin 14 of the wrist 18. The two bellows 20, 22 are spaced apart from each other in the right and left direction as seen in FIG. 1, in a direction perpendicular to the radial artery 34, when the main frame 10 of the instant apparatus is set in position on the wrist 18. If the levels of the air pressures applied to these two bellows 20, 22 are equal to each other, the presser member 32 pressed on the skin 14 is held substantially parallel to the surface of the skin 14. However, the presser member 32 is inclined relative to the skin 14 in a plane perpendicular to the artery 34, if the air pressures applied to the bellows 20, 22 are different from each other.

The main frame 10, and the housing member 38 of the presser member 32 both have a square shape as seen in the cross section of FIG. 2. Each of the four bellows 24, 26, 28 and 30 is disposed between the opposite inner and outer surfaces of the corresponding sides of the main frame 10 and the housing member 38. Described more specifically, each of the bellows 24, 26 is interposed between the corresponding sides of the main frame 10 and the housing member 38, which are spaced apart from each other in the direction perpendicular to the artery 34, when the main frame 10 is set in position on the wrist 18. On the other hand, each of the bellows 28 and 30 is interposed between the corresponding sides which are spaced apart from each other in the direction parallel to the artery 34. If the pressures of the air applied to the bellows 24, 26 through the third and fourth valves 68, 70 are equal to teach other, the presser member 32 is held in a substantially middle position within the main frame 10, in the direction perpendicular to the artery 34, i.e., in the right and left direction of FIG. 2. However, if the air pressures applied to these bellows 24, 26 are different, the presser member 32 is moved relative to the main frame 10 or to the skin 14 in the direction perpendicular to the artery 34. If the pressures of the air applied to the bellows 28, 30 through the fifth and sixth valves 72, 74 are equal to teach other, the presser member 32 is held in a substantially middle position within the main frame 10, in the direction parallel to the artery 34, i.e., in the vertical direction of FIG. 2. However, if the air pressures applied to these bellows 28, 30 are different, the presser member 32 is moved relative to the main frame 10 or to the skin 14 in the direction parallel to the artery 34.

The electric signals generated from the strain gauges 48, 50, 52 are applied to a control device 76 as shown in FIG. 4. This control device 76, which is constituted by a microcomputer in this specific embodiment, is adapted to apply controlled drive signals to the pressure regulating valves 64, 66, 68, 70, 72, 74, based on the electric signals received from the strain gauges 48, 50, 52, so that the air pressures to be applied to the respective bellows 20, 22, 24, 26, 28, 30 are suitably regulated. Further, the control device 76 is adapted to control a display and recording device 78, to indicate and record a pulse wave of the radial artery 34, based on the electric signal from the intermediate strain gauge 50.

The operation of the instant pulse wave detecting apparatus will be described.

Initially, the main frame 10 is attached to the wrist 18 by the straps 16, such that the presser member 32 is positioned right above the radial artery 34. At this time, it is desirable that the contact element 56 of the intermediate oscillating plate 44 assigned to sense the pulse wave of the artery 34 be exactly aligned with the artery 34. However, it is very difficult to establish an exact alignment of this intermediate oscillating plate 44 with the artery 34, if this is accomplished by way of visual inspection by the user.

Then, the control device 76 commences to control the first and second pressure regulating valves 64, 66, for applying the same air pressures to the bellows 20, 22, in order to force the bottom wall 36 and the contact elements 54, 56, 58 of the presser member 32 against the skin 14. As a result, the contact elements 54, 56, 58 are oscillated in response to blood pressure pulsations of the artery 34, whereby the strain gauges 48, 50, 52 produce electric signals indicative of their oscillatory motions, which represent the pulse wave of the artery 34.

Amplitudes of the electric signals produced by the three strain gauges 48, 50, 52 differ from each other, depending upon the positions of the pressed contact elements 54, 56, 58 relative to the artery 34. Certainly, the electric signal produced by one of the strain gauges 48, 50, 52 which is closest to the artery 34 has the largest amplitude. Since the intermediate strain gauge 50 is used to sense the pulse wave of the artery 34, the control device 76 operates to control the third and fourth pressure regulating valves 68, 70, based on the amplitudes of the electric signals received from the strain gauges 48, 50, 52, in order to adjust the air pressures applied to the bellows 24 and 26, and to thereby move the presser member 32 relative to the artery 34, to a position in which the electric signal from the intermediate strain gauge 50 has the largest amplitude, while the electric signals from the two outer strain gauges 48, 52 have comparatively low, substantially equal amplitudes. In this manner, the contact element 56 of the intermediate oscillating plate 44 is positioned right above the artery 34, for achieving accurate detection of the pulse wave of the artery 34.

The amplitude of the electric signal generated by the strain gauge 50 due to the oscillatory deformation of the contact element 56 thus positioned right above the radial artery 34, also varies depending upon the position of the presser member 32 in the direction parallel to the artery 34, and upon the specific posture of the presser member 32 relative to the artery, because of the presence of the radius and hypodermal tissue of the wrist 18. In the light of this fact, the control device 76 operates to control the fifth and sixth pressure regulating valves 72, 74, for adjusting the air pressures applied to the bellows 28, 30 and thereby moving the presser member 32 in the longitudinal direction of the artery 34, to a position in which the electric signal from the strain gauge 50 has the largest amplitude. Also, the first and second valves 64, 66 are controlled to adjust the pressures applied to the bellows 20, 22, for adjusting the posture or angle of inclination of the presser member 32 in a plane perpendicular to the artery 34, so that the electric signal from the strain gauge 50 has the largest amplitude. Thus, the positions of the contact element 56 in the directions perpendicular and parallel to the artery 34, and its posture relative to the skin 14, are adjusted relative to the main frame 10, so that the amplitude of the electric signal produced by the intermediate strain gauge 50 is the largest.

In some cases where the position of the main frame 10 relative to the wrist 18 is considerably misaligned with the artery 34 in the direction perpendicular to the artery 34, for example, the amplitude of the signal from the strain gauge 50 of the intermediate oscillating plate 44 cannot be larger than that of the strain gauge 48 or 52, even by moving the presser member 32 in the right and left direction of FIG. 1. In such cases, the control device 76 controls the first and second valves 64, 66 to adjust the pressures applied to the bellows 20, 22, in order to change the posture or inclination of the presser member 32 in the plane of FIG. 1 (perpendicular to the extending direction of the artery 34), so that the electric signal of the strain gauge 50 has the largest amplitude. If this adjustment does not permit the strain gauge 50 to have an electric signal having the largest amplitude, the control device 76 commands the display and recording device 78, to provide an indication of this fact, advising the user that the main frame 10 must be re-positioned on the wrist 18.

If the presser member 32 is moved while its bottom wall 36 is held pressed against the skin 14, the skin 14 may be displaced due to friction between the skin 14 and the bottom wall 36, causing inaccurate detection of the pulse wave of the artery 34. Therefore, where there exists a comparatively large friction force between the skin 14 and the bottom wall 36, it is preferred that the control device 76 be operated to reduce the air pressures applied to the bellows 20, 22, or stop the supply of the pressuzied air to these bellows, or alternatively connect the bellows 20, 22 to a vacuum source, for reducing the depression force of the presser member 32 to a lower, zero, or negative level, before the presser member 32 is moved relative to the skin 14. After this adjustment of the presser member 32 is completed, the presser member 32 is again depressed against the skin 14 by the bellows 20, 22, and the electric signals from the strain gauges 48, 50, 52 are received by the control device 76.

After the presser member 32 is thus oriented in the appropriate positions and posture relative to the skin 14, the air pressures applied to the bellows 20, 22 are equally raised or lowered, to adjust the depression force of the presser member 32 against the skin 14, so that the electric signal received from the strain gauge 50 has the larget amplitude. In this respect, it is noted that if an excessively large depression force is exerted on the presser member 32, the artery 34 is completely occluded and provides no pulse wave. On the other hand, the pulse wave to be transmitted to the contact element 56 is weak if the depression force is excessively small. Usually, the amplitude of the electric signal produced by the strain gauge 50 is the largest when the artery 34 depressed by the presser member 32 takes an oval form in the transverse cross section.

The electric signal produced by the strain gauge 50 of the thus oriented presser member 32 is continuously received by the control device 76, and the device 76 commands the display and recording device 78 to display and record a pulse wave of the artery 34 represented by the received signal. If necessary, the control device 76 is adapted to diagnose the working conditions of the heart of the subject based on the detected waveform, and/or determine the maximum and minimum (systolic and diastolic) blood pressures based on the maximum and minimum values of the pulse wave.

During this process of detection of the pulse wave, the control device 76 continues to compare the received electric signals from the three strain gauges 48, 50, 52 with each other, to adjust the air pressures applied to the bellows 24, 26, for moving the presser member 32 if the contact element 56 is dislocated due to movement of the wrist 18 of the subject, so that the contact element 56 is always held in the optimum position in the direction perpendicular to the artery 34. In the present embodiment wherein the three strain gauges 48, 50, 52 are provided, the direction in which the presser member 32 is dislocated can be readily detected, and the presser member 32 can be rapidly re-located into position.

It follows from the above detailed description that the positions and posture of the presser member 32 relative to the skin 14 are adjusted in the present embodiment, so as to hold the contact element 56 in an optimum position for detecting a pulse wave of the artery 34 with high accuracy. In particular, the detecting accuracy can be improved, because the instant embodiment is capable of adjusting the position of the presser member 32 in the longitudinal direction of the artery 34, and the posture of the presser member 32 relative to the skin 34, as well as the position of the presser member 32 in the direction perpendicular to the artery 34.

Further, since the contact element 56 is held in the optimum position by adjusting the positions and posture of the presser member 32, the contact elements 54, 56, 58 may have a larger size, than those used in the conventional detecting apparatus wherein an element for detecting the pulse wave is selected from among a multiplicity of contact elements which are not movable relative to the artery 34 once the apparatus is set. This means that the oscillating plates 44, 46, 48 having the contact elements 54, 56, 58, and the strain gauges 48, 50, 52 can be comparatively easily manufactured. Further, the relatively large strain gauges 48, 50, 52 assure comparatively higher detecting accuracy, than the conventionally used strain gauges or other converter means which are relatively small in size.

The comparatively high detecting accuracy of the instant detecting apparatus is also assured even when the presser member 32 is more or less dislocated due to movement of the subject, since the positions and posture of the presser member 32 are adjusted while the apparatus is in the process of detecting the pulse wave. In particular, based on the electric signals supplied from the three strain gauges 48, 50, 52, the control device 76 can readily determine the direction of dislocation of the presser member 32, and therefore rapidly re-orient the dislocated presser member 32.

In the present embodiment, the bellows 20, 22, 24, 26, 28 and 30, pressure regulating valves 64, 66, 68, 70, 72 and 74, and control device 76 cooperate to provide positioning means for moving the presser member 32 relative to the subject. Further, the bellows 20, 22, pressure regulating valves 64, 66 and control device 76 also function as pressing means for forcing the presser member 32 against the subject.

While the present invention has been described in its preferred embodiment, the invention may be otherwise embodied.

Figure 5:
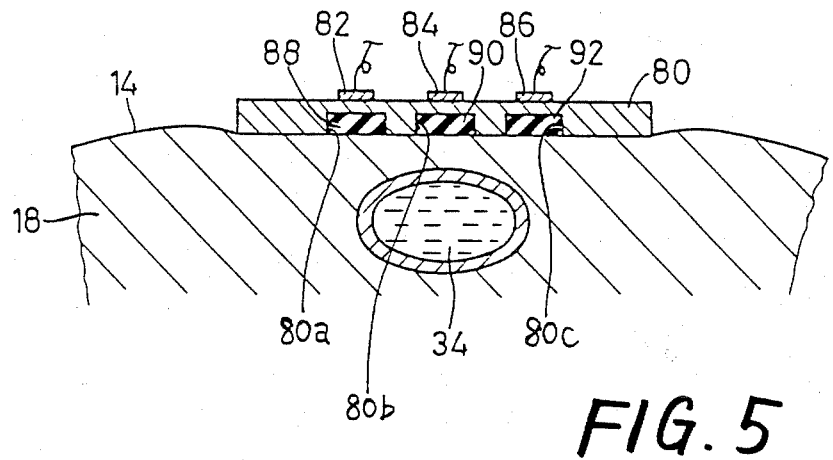
FIG. 5 is a fragmentary elevational view of another embodiment of the invention.

For instance, the strain gauges 48, 50, 52 adapted to sense the oscillatory deformation of the oscillating plates 42, 44, 46 may be semiconductor strain gauges, or may be replaced by various other means known for detecting a pulse wave. An example of an alternative detecting arrangement is illustrated in FIG. 5, in which a single-crystal silicon chip 80 is secured to the housing member 38 so as to form a bottom wall in place of the bottom wall 36 of the preceding embodiment. The semiconductor chip 80 is provided at its thin-walled portions with three piezoelectric elements 82, 84, 86. This silicon chip 80 is adapted such that blood pressure pulsations of the artery 34 are transmitted to the thin-walled portions and the corresponding piezoelectric elements 82, 84, 86 through three rubber fillers 88, 90, 92, respectively. More specifically, the thin-wall portions of the chip 80 define three recesses which are open in the outer surface of the chip. The rubber fillers 88, 90, 92 are secured to the chip 80 such that the fillers fill the respective recesses. Resulting oscillatory pressure vibrations of the thin-walled portions of the chip 80 are converted by the piezoelectric elements 82, 84, 86 into corresponding electric signals. In this modified embodiment of FIG. 5, the rubber fillers 88, 90, 92 correspond to the contact elements of the presser member. It is desirable that the diameter of each filler 88, 90, 92 be smaller than the diameter of the artery 34.

In the first embodiment, the pneumatically operated bellows 20, 22, 24, 26, 28 and 30 are used to move the presser member 32 relative to the main frame 10 along the mutually perpendicular three axes. However, these bellows may be replaced by feed screws driven by motors to position the presser member 32, or replaced by springs or elastomeric members to force the presser member 32 against the skin 14. Further, the principle of the present invention may be practiced, provided that the contact element 56 may be moved at least in the direction perpendicular to the artery 34, so as to be positioned right above the artery 34 and depressed against the skin 14.

It is also possible to provide a position sensor for detecting the position of the presser member 32, and determine a target position of the presser member 32 based on the electric signals from the strain gauges 48, 50, 52, so that the bellows 20, 22, 24, 26, 28, 30 are activated to move the presser member 32 to the determined target position.

Although the positions and posture of the presser member 32 are adjusted by controlling the pressures of the air to be supplied to the bellows 20, 22, 24, 26, 28, 30, it is possible to positively discharge the pressurized air from the bellows, for positioning or orienting the presser member 32.

In the first embodiment, the three oscillating plates 42, 44, 46 are used, and the pulse wave detection is effected based on the oscillatory deformation of the intermediate oscillating plate 44. However, the principle of the invention may be practiced even if a single oscillating plate is provided. Further, the pulse wave detection is not necessarily based on the oscillation of the intermediate plate 44, but may be achieved based on one of the three oscillating plates 42, 44, 46 whose output signal has the largest amplitude.

Also, the presser member 32 may include four or more oscillating plates, or the chip 80 may have four or more piezoelectric elements, as far as one of the plates or elements is brought into an optimum pulse wave detecting position by moving the presser member 32 or the chip 80 relative to the main frame 10 of the apparatus.

While the illustrated embodiments are adapted such that the positions and posture of the presser member 32 are monitored and adjusted even in the process of detecting the pulse wave, the principle of the invention may be practiced even where the adjustment of the positions and posture of the presser member 32 is effected only prior to the pulse wave detecting operation.

Although the positional adjustment of the presser member 32 in the illustrated embodiments is based on the amplitude of the electric signals generated by the strain gauges 48, 50, 52, the adjustment may be achieved with the intensity of the signals taken into account.

In the first embodiment, each oscillating plates 42, 44, 46 has the single strain gauge 48, 50, 52 so that the deformation of the plate is converted into an electric signal. However, each oscillating plate may have two or four strain gauges arranged in a bridge circuit to provide a single electric signal.

While it is preferable that the diameter of the contact elements 54, 56, 58, or the diameter of the rubber fillers 88, 90, 92 is smaller than the diameter of the artery 34, it is possible that the diameter of these contact elements or rubber fillers exceeds that of the artery 34. Further, the contact elements or fillers may have a suitable configuration other than a cylinder or disc.

Although the illustrated embodiments are adapted to detect the pulse wave of the radial artery 34, the present invention may be embodied as an apparatus for detecting a pulse wave of the other arterial vessels, such as the carotid artery.

It is to be understood that the present invention may be embodied with various other changes, modifications and improvements which may occur to those skilled in the art, without departing from the spirit and scope of the invention defined in the following claims.

What is claimed is:

1. A pulse wave detecting apparatus for detecting a blood pressure pulse wave of an arterial vessel of a subject, based on an oscillatory motion of at least one contact element which is adapted to be depressed against a surface of a body member of the subject, such that said at least one contact element is oscillated in response to the pulsation of the arterial vessel, said detecting apparatus comprising:

a main frame for supporting said at least one contact element such that said at least one contact element is movable relative to said main frame, said main frame being attached to said surface of the body member;

positioning means operable at least for moving said at least one contact element relative to and along said surface, in a direction perpendicular to a direction of extension of said arterial vessel, to thereby locate one of said at least one contact element right above said arterial vessel; and pressing means for moving said at least one contact element relative to said main frame, in a direction toward said surface, for forcing said at least one contact element against said surface.

2. A pulse wave detecting apparatus according to claim 1, wherein said at least one contact element consists of at least three contact elements which are arranged in a plane parallel to said surface, in spaced-apart relation with each other in said direction perpendicular to said arterial vessel, said positioning means being operable to position an intermediate one of said at least three contact elements right above said arterial vessel, based on the oscillatory motions of said at least three contact elements.

3. A pulse wave detecting apparatus according to claim 1, wherein said positioning means is also operable for moving said at least one contact element along said surface in a direction parallel to said direction of extension of said arterial vessel, and for adjusting an angle of inclination of said at least one contact element relative to said surface in a plane perpendicular to said direction of extension of said arterial vessel.

4. A pulse wave detecting apparatus according to claim 1, further comprising a presser member which includes (a) a housing structure movably supported and accommodated within said main frame, (b) at least one oscillating plate fixedly disposed within said housing structure, and (c) at least one strain gauge provided on said at least one oscillating plate, respectively, said housing structure including a bottom wall which has at least one hole formed therethrough, each of said at least one contact element extending through a corresponding one of said at least one hole and secured to a corresponding one of said at least one oscillating plate, such that said each contact element is movable in said corresponding one hole and exposed at a free end thereof for contact with said surface of said body member, said pressing means being operable to move said housing structure toward said surface and thereby press said free end of said each contact element against said surface.

5. A pulse wave detecting apparatus according to claim 4, wherein said housing structure includes a boxlike housing member having said bottom wall, and further includes a lid member which closes an opening remote from said bottom wall.

6. A pulse wave detecting apparatus according to claim 5, wherein said pressing means includes bellows interposed between an inner surface of said main frame and said lid member of said housing structure of said presser member, to force said housing structure against said surface of said body member.

7. A pulse wave detecting apparatus according to claim 4, wherein said positioning means includes bellows interposed between inner surfaces of said main frame, and opposite outer surfaces of said housing structure, to move said presser member along said surface in said direction perpendicular to said direction of extension of said arterial vessel.

8. A pulse wave detecting apparatus according to claim 7, wherein said positioning means further includes bellows interposed between an outer surface of a top wall of said housing structure remote from said bottom wall, and an opposite inner surface of said main frame, to change an angle of inclination of said presser member with respect to said surface of said body member in a plane perpendicular to said direction of extension of said arterial vessel.

9. A pulse wave detecting apparatus according to claim 4, wherein said each contact element consists of a cylindrical member which has a diameter smaller than a diameter of said arterial vessel.

10. A pulse wave detecting apparatus according to claim 1, further comprising a presser member which includes (a) a housing structure movably supported and accommodated within said main frame, (b) a semiconductor chip attached to said housing structure so as to form a bottom wall of said housing structure, said semiconductor chip having at least one thin-walled portion which defines a recess open in an outer surface of said bottom wall, and (c) at least one piezoelectric element provided on said at least one thin-wall portion of said semiconductor chip, respectively, said at least one contact element consisting of at least one rubber filler each of which fills said recess in said at least one thin-walled portion of said semiconductor chip, such that the blood pressure pulse wave of said arterial vessel is transmitted to said at least one thin-walled portion of said semiconductor chip via said at least one rubber filler, said pressing means being operable to move said housing structure toward said surface of said body member and thereby press said at least one rubber filler against said surface.

11. A pulse wave detecting device according to claim 10, wherein each of said at least one rubber filler has a diameter smaller than that of said arterial vessel.

12. A pulse wave detecting device according to claim 1, wherein said positioning means includes pneumatically operated actuators for moving said at least one contact element in the direction perpendicular to said direction of extension of said arterial vessel, and pressure regulating valves connected to said actuators to control air pressures to be applied to said actuators, said positioning means further comprising control means for controlling said pressure regulating valves.

* * * * *